(12) United States Patent
Noftsker

(10) Patent No.: US 10,751,505 B2
(45) Date of Patent: Aug. 25, 2020

(54) METHOD FOR STIMULATING NEURAL ACTIVITY

(71) Applicant: SYMBOLICS INC., Lincoln, MA (US)

(72) Inventor: Russell Noftsker, North Billerica, MA (US)

(73) Assignee: SYMBOLICS INC., Lincoln, MA (US)

( * ) Notice: Subject to any disclaimer, the term of this patent is extended or adjusted under 35 U.S.C. 154(b) by 0 days.

(21) Appl. No.: 16/804,143

(22) Filed: Feb. 28, 2020

(65) Prior Publication Data

US 2020/0197658 A1    Jun. 25, 2020

Related U.S. Application Data

(63) Continuation of application No. 16/691,901, filed on Nov. 22, 2019, now Pat. No. 10,610,662, which is a continuation of application No. 16/260,430, filed on Jan. 29, 2019, now Pat. No. 10,518,063.

(60) Provisional application No. 62/756,992, filed on Nov. 7, 2018.

(51) Int. Cl.
*A61M 21/02* (2006.01)
*A61N 5/06* (2006.01)
*A61B 5/00* (2006.01)
*A61M 21/00* (2006.01)

(52) U.S. Cl.
CPC ........... *A61M 21/02* (2013.01); *A61B 5/4064* (2013.01); *A61N 5/0618* (2013.01); *A61N 5/0622* (2013.01); *A61M 2021/0044* (2013.01); *A61N 2005/0663* (2013.01)

(58) Field of Classification Search
CPC .......... A61M 2021/0044; A61M 21/02; A61M 2205/505
See application file for complete search history.

(56) References Cited

U.S. PATENT DOCUMENTS

| | | |
|---|---|---|
| 10,518,063 B1 | 12/2019 | Noftsker |
| 2010/0094702 A1 | 4/2010 | Silberstein |
| 2013/0267759 A1 | 10/2013 | Jin |
| 2014/0058483 A1 | 2/2014 | Zao |
| 2017/0143934 A1 | 5/2017 | Tsai et al. |
| 2018/0133504 A1 | 5/2018 | Malchano |

OTHER PUBLICATIONS

Singer er al., "Noninvasive 40 Hz light flicker to recruit microglia and reduce amyloid bata load"; Nature Protocol, vol. 13, Aug. 2018, pp. 1850-1868.

*Primary Examiner* — Christine H Matthews
(74) *Attorney, Agent, or Firm* — Norris McLaughlin, P.A.

(57) ABSTRACT

A method for stimulating neural activity in the brain of a user of an apparatus with a display screen by causing at least one portion of the display screen to flicker in a controlled manner and utilizing the apparatus to measure an effect on a user exposed to the flicker for a time.

27 Claims, 5 Drawing Sheets

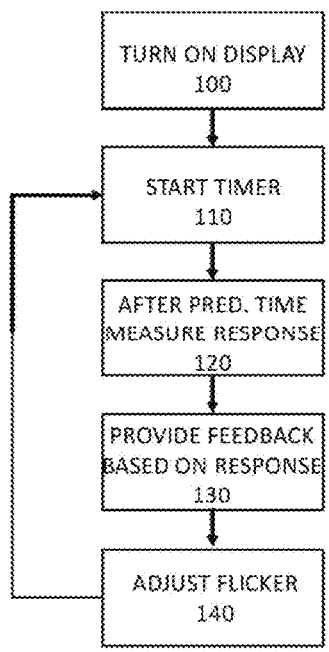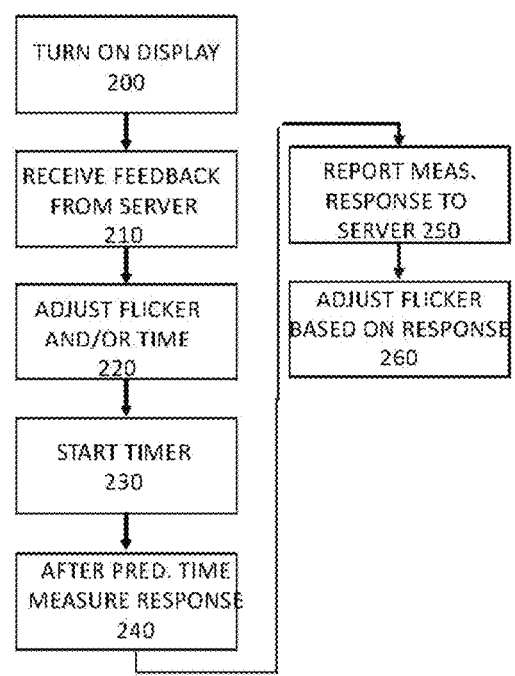
FIGURE 5
FIGURE 6

METHOD FOR STIMULATING NEURAL ACTIVITY

PRIORITY CLAIM

This application is a continuation of U.S. Nonprovisional patent application Ser. No. 16/691,901, filed Nov. 22, 2019, now U.S. Pat. No. 10,518,063, which is, in turn, a continuation of U.S. Nonprovisional patent application Ser. No. 16/260,430, filed Jan. 29, 2019, which, in turn, claims priority of U.S. Provisional Patent Application Ser. No. 62/756,992, filed Nov. 7, 2018, the entire contents of which patent applications are hereby incorporated herein by reference.

BACKGROUND OF THE INVENTION

The present invention relates to biomedical engineering and in particular to a method and apparatus for effecting neural stimulation.

In recent years smartphones, such as the Apple iPhone and Android phones such as the Samsung Galaxy, have become ubiquitous. Many complain that people spend a lot of time looking at the display screens of these phones as well as tablets, such as the Apple iPad and the Samsung Galaxy tablet. In addition, with the increasing processing power of gaming devices such as the Nintendo Switch, the Microsoft Xbox and the Sony PlayStation, gamers can spend hours in front of the display screens of these devices. There is some concern, including within the medical community, that spending so much time exposed to the display screens of these devices will have deleterious effects on the users.

Recently, neural scientists have found that exposure to a controlled flickering of light will stimulate neural activity in the brains of mice. The basis for this stimulation is the inducing of microglia into an engulfing state which facilitates the transport of amyloid beta away from an area where it interferes with brain function. This is described in an article entitled *Noninvasive 40-Hz light flicker to recruit microglia and reduce amyloid beta load* by Singer et al., Nature Protocols, Vol. 13, Aug. 2, 2018, pp. 1850-1868 and in Published U.S. Application 2017/0143934 published May 25, 2017, the disclosures of both of which are hereby incorporated herein by reference. In the article, the authors disclose that they "recently showed that using noninvasive exposure to 40-Hz white-light (4,000 K) flicker to drive 40-Hz neural activity transforms microglia into an engulfing state and reduces amyloid beta, a peptide thought to initiate neurotoxic events in Alzheimer's disease". In addition, research has shown that exposure to bluer light near the end of a person's circadian rhythm delays the onset of natural sleep more than does exposure to redder light.

SUMMARY OF THE INVENTION

The main object of the present invention is to use the seemingly disadvantageous effects of long display screen exposure with the advantageous effects of light flicker to stimulate neural activity.

As used herein, the term "color temperature" is used with its ordinary meaning within the scientific community, and is expressed in degrees Kelvin, with the symbol "K" standing for "Kelvin", e.g., "4000° K". As used herein, the term "color", when not used as part of the term "color temperature", is used to refer to the subjective perception by the viewer of one or more color temperatures viewed simultaneously, and such perception typically is given a name, e.g., "red-orange". As used herein, the term "flicker" is used to refer to a series of pulses of electromagnetic radiation with periods of time between each two consecutive pulses.

The above and other objects of the invention are achieved in accordance with the invention by a method and apparatus for stimulating neural activity in the brain of a user of an apparatus with a display screen, by causing at least one portion of the display screen to flicker in a controlled manner and utilizing the same apparatus to measure the effect on a user exposed to the flicker for an amount of time. The time can be a randomly-determined time or can be a predetermined time. The time can be based upon the time the display screen is on or based upon the time the user is exposed to the flicker. The time can be a time interval or a time of day. For time of day, the color of the flicker can be moved to a redder range to avoid interfering with the circadian sleep cycle.

In a preferred embodiment, the apparatus for stimulating neural activity in the brain of a user comprises a display screen, a flicker control processor to cause at least one portion of the display screen to flicker in a controlled manner, and an effect processor for measuring the effect on a user exposed to the display screen flicker for an amount of time. The light flicker to stimulate neural activity is preferably the high rate light flicker in the normally unnoticed range of movies (24 Hz), TV's (25, 30, 50, & 60 Hz), and fluorescent/LED lights (30, 50, & 60 Hz). Preferably, feedback is used to enhance any detectable advantageous effects which may result from controlling illumination flicker timing, color, intensity and scene location parameters. The flicker control processor and the effect processor can be software or purpose-built circuitry.

In the method and apparatus, the apparatus can be any device that displays information or is used for entertainment and is preferably a smartphone such as an iPhone or an Android phone, a smart watch such as an Apple Watch, a tablet such as an iPad or an Android tablet, a laptop computer such as a Mac, a Windows computer or a Chromebook, an e-reader such as a Kindle, a Nook, a PDA, a gaming device such as a Nintendo gaming device such as the Switch, an Xbox, or a Sony PlayStation, a television, or a purpose-built device (i.e., a device whose principal function is to expose a user to light flicker and to measure its effect on the user). Additionally, a purpose-built device can be a fanciful device such as a doll or a plush toy with a display screen that flickers, for example the eyes or accoutrements of the doll or a stuffed animal. In each of the embodiments, the display screen is preferably a touch-screen display.

The at least one portion of the display screen that has the controlled flicker can be anywhere on the display screen and is preferably around an edge of the display screen, along a side of the display screen, along a top portion of the display screen, along a bottom portion of the display screen, in a middle portion of the display screen, in a pattern on the display screen, in a random portion of the display screen, in a predictably movable pattern on the display screen, in a randomly movable pattern on the display screen, and/or in a user selected portion on the display screen. The at least one portion of the display screen may be any portion of the display screen from just over 0% to 100% (i.e., the entire display screen). Alternatively, the entire background of the text on the display screen can flicker, all text and other information on the display screen can flicker, or the entire display screen can flicker. In a preferred embodiment, where a game, video or application is running, the flickering portion or portions are configured so as not to interfere with any game, video, or application being run on the device. Preferably 5-50% percent of the display screen will flicker, more preferably 10-30% and most preferably 15-25%. In a purpose-built device or a fanciful design device, the flickering portion is preferably 50-100%. In other embodiments, the flicker can be in the on-screen information or entertainment being presented on the display screen such as in the background or as part of the illumination of the information or entertainment and would be a significant percentage of the display screen, e.g., greater than 20% and preferably 80-100% of the display screen.

In a preferred embodiment, during the flickering at least one of waveform, color, color temperature, illumination, saturation, contrast, and brightness of at least one pulse is varied during the pulse. In another preferred embodiment, within the flickering at least two pulses have different durations. In yet another preferred embodiment, within the flickering the period of time between one pair of consecutive pulses is different from the period of time between at least one other pair of consecutive pulses.

In yet another preferred embodiment of the method, a position, flicker rate, off/on contrast ratio, illumination level, waveform, and/or color of the at least one portion can be adjusted by feedback, for example, by feedback from the user, or by feedback from a plurality of users. A position, flicker rate, off/on contrast ratio, illumination level, waveform, and/or color of the at least one portion can be adjusted based upon a response from the user or upon responses from a plurality of users. A position, flicker rate, off/on contrast ratio, illumination level, waveform, and/or color of the at least one portion can be adjusted based upon measurement of a reaction of the user or upon measurement of the reactions of a plurality of users.

In a preferred embodiment of the apparatus, a flicker control processor can adjust a position, the flicker rate, off/on contrast ratio, illumination level, waveform, and/or color of the at least one portion using feedback, for example, using feedback from the user, or by using feedback from a plurality of users. The flicker control processor can adjust a position, flicker rate, off/on contrast ratio, illumination level, waveform, and/or color of the at least one portion based upon a response from the user or upon responses from a plurality of users. The flicker control processor can adjust a position, flicker rate, off/on contrast ratio, illumination level, waveform, and/or color of the at least one portion based upon based upon measurement of a reaction of the user, or upon measurement of the reactions of a plurality of users.

In another preferred embodiment of the method, the time can be a predetermined time including a start time and a stop time and can be set by the user. The time exposed to the flicker can be determined based upon a response or responses from the user to prompts on the display screen or audio prompts. The predetermined time can be set by feedback, for example, the predetermined time can be set by feedback based upon a response or responses from the user or upon responses from a plurality of users. The predetermined time can be set by feedback based upon measurement of a reaction or reactions of the user, or upon measurement of the reactions of a plurality of users.

In another preferred embodiment of the apparatus, the apparatus further comprises a timer, which can be implemented in software or by a purpose-built circuit, for determining the predetermined time, and wherein the predetermined time can be set by the user. The predetermined time can be based upon the time the display screen is on, or the predetermined time can be based upon the time the user is exposed to the flicker. The time exposed to the flicker can be set by feedback, for example, the time exposed to the flicker can be set by feedback based upon a response or responses from the user or upon responses from a plurality of users. The time exposed to the flicker can be set by feedback based upon measurement of a reaction or reactions of the user, or upon measurement of the reactions of a plurality of users. The time exposed to the flicker can be based upon a response or responses from the user to prompts on the display screen or audio prompts.

In still another preferred embodiment of the method, the flicker has an adjustable frequency that can be adjusted, preferably in the range of 35-45 Hz. The flicker has a color temperature and the flicker can be adjusted by changing the color temperature, preferably by changing the color temperature in the range of 4000° K±10%. The color itself also can be changed to a color across the visible spectrum. The flicker has a saturation and the flicker can be adjusted by changing the saturation. The flicker has a contrast and the flicker can be adjusted by changing the contrast, preferably relative to other portions of the display screen. The flicker has a pulse shape and the flicker can be adjusted by changing the pulse shape. The flicker has a duty cycle of preferably 50% and the flicker can be adjusted by changing the duty cycle in a range of 25-75% and most preferable 40-60%. The flicker can be adjusted by the user. The flicker can be adjusted by feedback, for example, the flicker can be adjusted by feedback based upon a response or responses from the user, or upon responses from a plurality of users. The flicker can be adjusted by feedback based upon measurement of a reaction or reactions of the user, or upon measurement of the reactions of a plurality of users. In addition, the flicker can be adjusted by feedback based upon the gender of the user, the race of the user, the ethnicity of the user, the age of the user, a medical condition of the user, and/or another biological parameter of the user (e.g., natural hair color, eye color, color blindness, epilepsy).

In still another preferred embodiment of the apparatus, wherein the flicker has a frequency and a flicker control processor is provided to adjust the flicker by changing the frequency, preferably by changing the frequency in the range of 35-45 Hz. In another embodiment, the frequency is in the range of human brain gamma waves, usually 25 to 100 Hz, with 40 Hz being the most typical, and such frequency would be the starting point first used when being utilized with new users. The flicker control processor can adjust the flicker by changing the color temperature, preferably in the range of 4000° K±10%. In another embodiment, the color is changed within the human visual sensitivity range normally between 380 nm and 770 nm. The flicker control processor can change the color in response to the time of day or the user's circadian rhythm cycle. The flicker control processor can adjust the flicker by changing the saturation, the flicker control processor can adjust the flicker by changing the contrast, the flicker control processor can adjust the flicker by adjusting the pulse shape, and/or the flicker control processor can adjust the flicker by changing the duty cycle which is preferably 50% and which can be adjusted in the range of preferably 25-75% and most preferable 40-60%. The flicker control processor can adjust the flicker in response to an input by the user, in response to feedback, in response to measurement of a reaction or reactions of the user, based upon the responses of a plurality of users, and/or based upon the gender of the user, the race of the user, the ethnicity of the user, the age of the user, a medical condition of the user, and/or another biological parameter of the user (e.g., natural hair color, eye color, color blindness, epilepsy).

In yet another embodiment of the method, the apparatus is a smartphone and a response from the user can be evaluated by a smartphone app running on the smartphone.

The response can be to a prompt on the display screen, or to a test presented on the display screen. In yet another embodiment of the method, the apparatus is a smartphone and a smartphone app running on the smartphone can measure a reaction or reactions of the user. The reaction measured can be the reaction-time of the user, or the speed of use of the keyboard by the user. In yet another embodiment of the apparatus, the apparatus is a smartphone and the effect processor runs a smartphone app running on the smartphone to measure effect, wherein the effect processor can measure a reaction by the user to a prompt on the display screen, wherein the effect processor can measure by results on a test presented to the user on the display screen, including a test of reaction time, and/or wherein the effect processor can measure by the speed of use by the user of the keyboard of the display screen.

In a preferred embodiment of the invention, the flicker rate starts at 40 Hz, a color temperature of 4000° K and a duty cycle of 50%.

These and other features of the present invention will be described in more detail with respect to the following drawing wherein:

BRIEF DESCRIPTION OF THE DRAWINGS

FIG. 5 is a flowchart of a method according to the present invention; and

FIG. 6 is a flowchart of another method according to the present invention.

DETAILED DESCRIPTION OF THE PREFERRED EMBODIMENTS

Referring now to FIGS. 1A-1F, the present invention is advantageously embodied in a smartphone 1, such as the iPhone shown therein. The smartphone is particularly advantageous, because the operating system permits an application designer to control the display screen and select a portion or portions thereof to make it flicker at a selected frequency, to adjust its position, its color temperature, its color, its saturation, its contrast, its brightness, the duty cycle of the flickering, and the waveform used to create the flickering. In addition, IOS 12 for the iPhone has the capability to measure the amount of time the user has the display screen on, and to measure the amount of time that a user is viewing a particular app. In addition, there are many apps available for a smartphone that can be used to measure mental acuity and response time. Examples of such apps are Lumosity, Tricky Test, and Peak—Brain Training. As a result, many of the requirements for the apparatus according to the present invention for carrying out the method according to the present invention are available on a smartphone, although the combinations thereof as set forth in the claims are novel.

The present invention is also particularly advantageously embodied in a gaming device such as a Nintendo Switch, a Microsoft Xbox or a Sony PlayStation, since users spend a great deal of time exposed to the display screen, the devices provide a record of time played, and the games played on the devices measure reaction time of a user to different visual and audio stimuli.

As shown in FIGS. 1A-1F, the display screen 2 has areas 3A-3F that flicker at least during the time that the user is exposed to the display screen, e.g., playing a game, watching a video, reading text, etc. The flickering areas are around the edge 3A, on the sides 3D and 3E, on the top and bottom 3C and 3B or in the corners 3F. The flickering areas are preferably positioned so as not to interfere with the operation of any app or video.

Figures 1A, 1B, 1C:
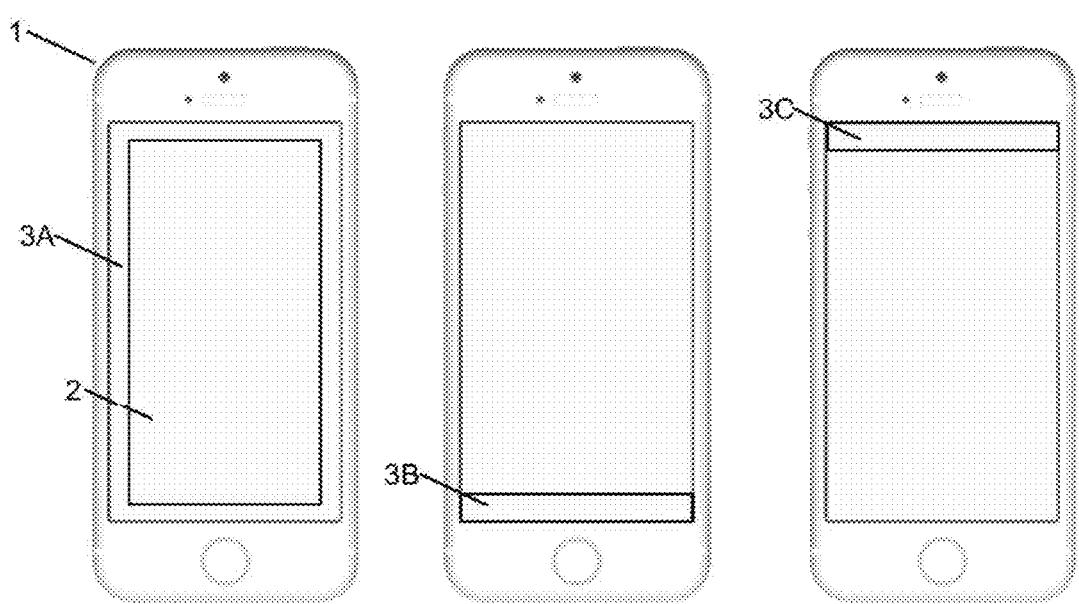
FIGS. 1A-1F show examples of different light flickering positions of the display screen of a smartphone in accordance with the invention.
Figure 1D:
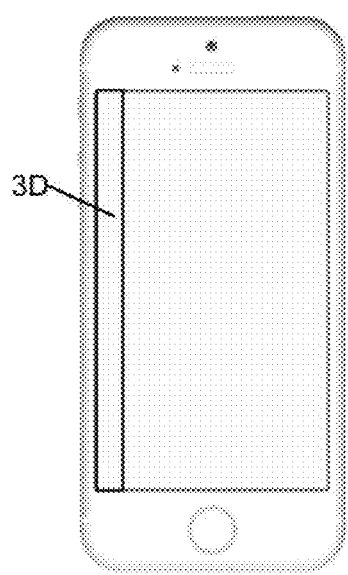
Figure 1E:
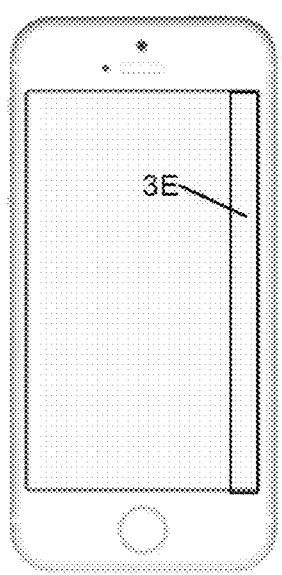
Figure 1F:
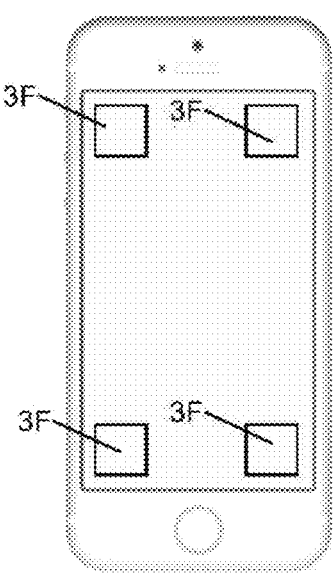
Figure 2:
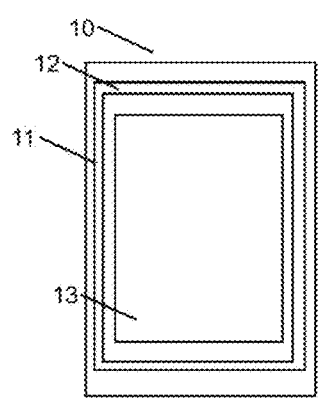
FIG. 2 shows the light flickering portion on the display screen of an e-reader.

FIG. 2 shows an e-reader 10, such as an Amazon Kindle, with a display screen 11 having a text portion 13 surrounded by a flickering area 12. Alternatively, the entire background of the text on the display screen can flicker, all text and other information on the display screen can flicker, or the entire display screen can flicker.

Figure 3:
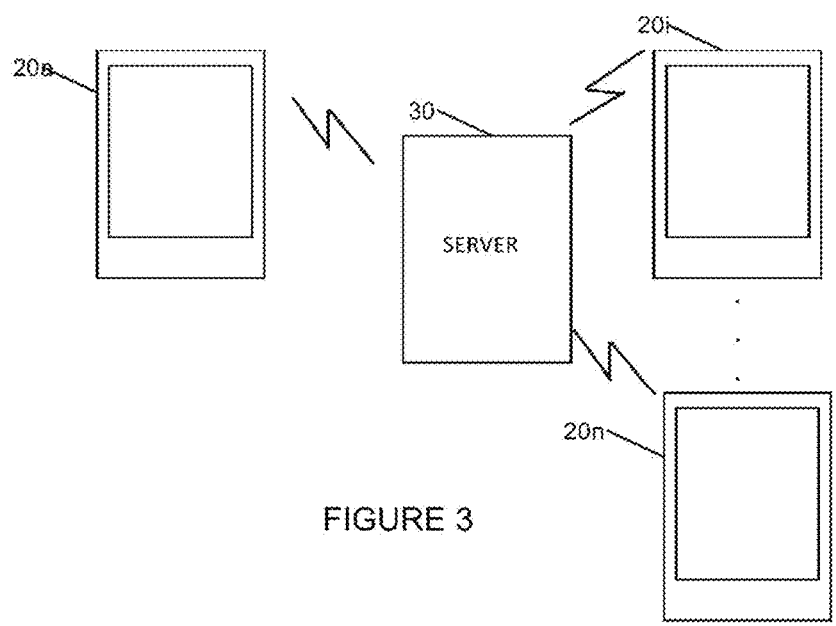
FIG. 3 shows a network for proving feedback in accordance with the invention.

FIG. 3 shows a network using apparatus in accordance with the invention. Tablets 20a and 20i-20n, such as the Apple iPad and the Samsung Galaxy are wirelessly in communication with server 30. The server 30 keeps track in a database of the display screen exposure time of each user, the results of the responses of the users, and the measurement of the reactions of the users. Alternatively, a device 20i can keep a local database record of the display screen exposure time of each user and process the results in software before sending the results to the server. The results of the responses of the users, and the measurement of the reactions of the users on the device itself can be sent to the server. The data in the database with respect to a user or of a plurality of users can be used as feedback to change parameters of the flickering, such as frequency, color temperature, color, saturation, contrast, brightness, position, percentage of display screen, etc. The server 30 can analyze the data of many users to determine which parameters most affect a particular user and provide feedback accordingly. The feedback can be based upon the gender of the user, the race of the user, the ethnicity of the user, the age of the user, a medical condition of the user, and/or another biological parameter of the user (e.g., natural hair color, eye color, color blindness, epilepsy).

Figure 4:
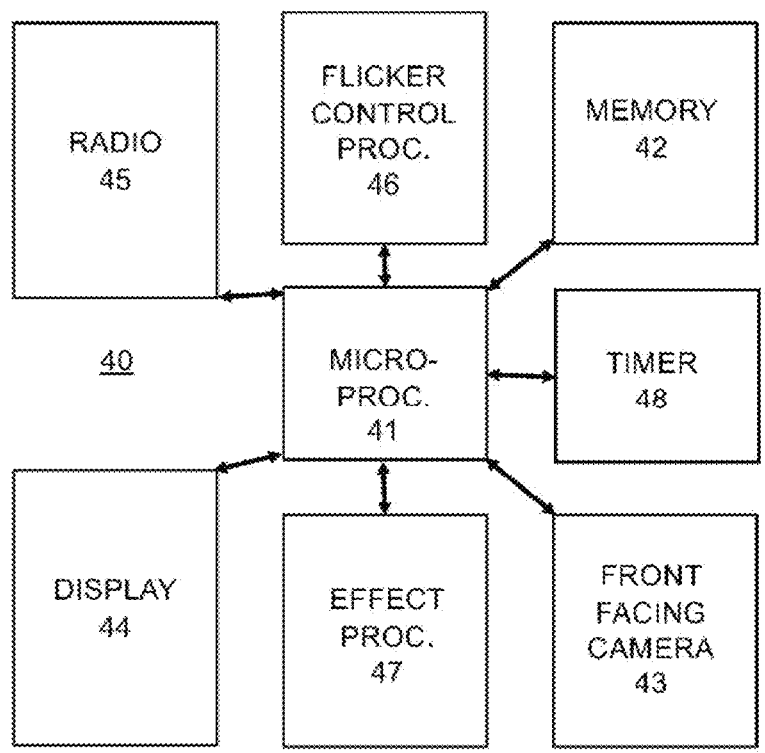
FIG. 4 is a block diagram of circuitry for an apparatus for carrying out the method according to the present invention.

FIG. 4 is a block diagram of the functional elements of a device 40 in accordance with the invention for a carrying out the method according to the invention. In FIG. 4, a main processor 41 is a microprocessor which interacts with memory 42, which is a ROM, RAM or combination of the ROM and RAM, for program instructions. Memory 42 is also available to store settings for the flicker parameters and to store a database of user records. The processor 41 also interacts with the display 44, the radio 45 and the front facing camera 43. The display of the device includes a display screen and conventional circuitry for driving the display screen. The front facing camera is preferably of the type used for Face ID on an iPhone or Android phone, because it is capable of determining whether or not the user is looking at the display screen. The radio 45 is preferably a Wi-Fi radio, a Bluetooth radio, and/or a cellular (LTE or 5G) radio or a combination thereof for communicating with server 30. The device 40 also includes a timer 48, a flicker control processor 46 and an effect processor 47. These modules can be hardware or software based in processor 41 and while they are shown as separate elements, they can be embodied in one or more processors and implemented in software. The timer 48 measures the time that the display screen is on and/or the time the user is exposed to the display screen, for example based upon the front facing camera 43 or based upon audio prompts or visual prompts to the user on the display screen to see if the user is actually looking at the display screen. The flicker control processor can adjust the parameters of the flickering which can be set by the user, can be based upon feedback from data stored in the memory or it can be based upon feedback from the server 30. The effect processor 47 measures the effect on a user of visual and/or audio prompts. The measuring can be of reaction time, of results on memory tests, of results on mental acuity tests, of speed tests, etc.

FIGS. 5 and 6 are flowcharts of methods according to the present invention. In the flowchart of FIG. 5, the first step 100 is to turn on the display screen. The turning on of the display screen leads to the second step 110 of starting the timer. While it is desirable to time the actual exposure of the user to the flickering, the time that the display screen undergoes controlled flickering is a good approximation. Preferably, a front facing camera can detect that the eyes of the user are on the display screen. Alternatively, visual or audio prompts can require an action by the user to show that the user is paying attention to the display screen. After a predetermined time of exposure to the display screen, in step 120 an effect on a user is measured. This measurement can take different forms. For example, the effect that is measured is the reaction time of the user to an audio or visual prompt on the display screen. The measurement can be in the form of the results of a memory test displayed on the display screen of the display. Alternatively, a logic test can be displayed on the display screen. Preferably, one of many mental acuity tests that are available as apps for smartphones and other similar devices can be used as a measure. After the effect is measured, in step 130 feedback can be provided. For example, if the measured effect shows improvement from a previous measurement, the flicker may remain unchanged. If on the other hand there is no improvement, the flicker can be adjusted in step 140. Alternatively, the flicker can be adjusted even if there is an improvement, or the flicker may not be adjusted even if no improvement is measured. After there is or is not an adjustment, the timer is started again in step 110 and the process is repeated as long as the display screen is on. The times and parameters are preferably maintained in storage for review at a later time.

The method of FIG. 6 starts with turning on the display screen in step 200. In this embodiment the device receives feedback from the server 30. This feedback can be based upon data received from other users and in particular from users where there was an improvement in the measured effects over time. This feedback can be used to adjust one or more parameters relating to flickering including color temperature, color, frequency, contrast, saturation, brightness, duty cycle, and pulse shape. The feedback can be based upon the gender of the user, the race of the user, the ethnicity of the user, the age of the user, a medical condition of the user, and/or another biological parameter of the user (e.g., natural hair color, eye color, color blindness, epilepsy), where persons having similar characteristics have shown desired changes in measured effects. Upon receiving this feedback, the flicker and/or the predetermined time of exposure can be adjusted in step 220. The timer is then started in step 230 and after the adjusted predetermined time in step 240, an effect is measured. Thereafter, the measured effect is reported to the server 30 in step 250. The flicker can then be readjusted in step 260 and the process can be repeated.

The display screen for use with the present invention is preferably an LCD display screen or discrete LED light emitters. Alternatively, the display screen can be an LED or OLED display screen.

A user interface on the display screen of the apparatus is preferably an application program interface (API) such as a local API, web API or program API and, alternatively, can be a network interface controller that connects a computer to a computer network or a virtual network interface connecting a computer to a virtual private network.

Network shown in FIG. 3 is preferably a communications network using one or more commercial communications protocols, such as TCP/IP, FTP, UPnP, NFS, or CIFS. The network can be wireless or wired, including a local area network (LAN), a wide-area network (WAN), a virtual private network (VPN), the internet, an intranet, an extranet, a public switched telephone network (PSTN), a cellular network, a satellite communications network, an infrared network, another type of wireless network, and the like, or a combination of the foregoing.

An example of the present invention can include a database formed from a variety of data stores and other memory or storage media. These components can reside in one or more of the servers, as discussed above, or may reside in a network of the servers. Alternatively, the database can be stored locally and maintained on the user's smartphone, tablet, computer, or other storage device. In certain embodiments, the information may reside in a storage-area network (SAN). Similarly, files for performing the functions attributed to the computers, servers or other network devices discussed above may be stored locally and/or remotely, as appropriate. Each computing system described above, including the client devices, may incorporate hardware elements that are electrically coupled via data/control/and power buses. For example, one or more processors in such computing systems may be central processing units (CPU) for one or more of the client devices. The client devices may further include at least one user input device (e.g., a mouse, joystick, keyboard, controller, keypad, or touch-sensitive display screen) and at least one output device (e.g., a display, a printer, a speaker, or a device which itself is designed to provide electrical stimulation to the brain, such as transcranial direct-current stimulation devices and transcranial magnetic stimulation devices. Such client devices may also include one or more storage devices, including disk drives, optical storage devices and solid-state storage devices such as a random-access memory (RAM) or a read-only memory (ROM), as well as removable media devices, memory cards, flash cards, storage devices utilizing biological media (e.g., DNA), etc.

The computer systems discussed above also can include computer-readable storage media reader, communications devices (e.g., modems, network cards (wireless or wired), or infrared communication devices) and memory, as previously described. The computer-readable storage media reader is connectable or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements stored within at least one working memory device, including an operating system and application programs such as a client application or web browser. It should be appreciated that alternate embodiments may have numerous variations from that described above. For example, customized hardware also might be used, and/or particular elements might be implemented in hardware, in software (including portable software, such as applets), or in both. Further, connection to other computing devices such as network input/output devices may be employed.

Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage, other magnetic storage devices, or any other medium, including biological media such as DNA, which can be used to store the desired information and which can be accessed by a system device. Based upon the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

While various embodiments of the present disclosure have been described above, it should be understood that they have been presented by way of example only, and not of limitation. Likewise, the various diagrams may depict an example architectural or other configuration for the disclosure, which is done to aid in understanding the features and functionality that can be included in the disclosure. The disclosure is not restricted to the illustrated example architectures and configurations, but the desired features can be implemented using a variety of alternative architectures and configurations. Indeed, it will be apparent to one of skill in the art how alternative functional, logical, or physical partitioning and configurations can be implemented to implement the desired features of the present disclosure. For example, while a single server and a processor are illustrated, the server functions can be distributed over a number of servers and processors. Additionally, with regard to flow diagrams, operational descriptions, and method claims, the order in which the steps are presented herein shall not mandate that the steps of the various embodiments be implemented in the order presented, unless the context dictates otherwise.

Although the disclosure is described above in terms of various example embodiments and implementations, it should be understood that the various features, aspects, and functionality described in one or more of the individual embodiments are not limited in their applicability to the particular embodiment with which they are described, but instead can be applied, alone or in various combinations, to one or more of the other embodiments of the disclosure, whether or not such embodiments are described, and whether or not such features are presented as being a part of a described embodiment. Thus, the breadth and scope of the present disclosure should not be limited by any of the above-described example embodiments, and it will be understood by those skilled in the art that various changes and modifications to the previous descriptions may be made within the scope of the claims.

What is claimed is:

1. A method for stimulating neural activity in the brain of a user of a smartphone with a display screen and that is capable of running apps, comprising the steps of:
   a. causing at least one portion of the display screen to flicker in a controlled manner, wherein the display screen is a touch-screen display;
   b. exposing the user of the smartphone to the flicker during an exposure time thereby producing an effect on the brain of the user; and
   c. adjusting the flicker by an app that is running on the smartphone, wherein the app adjusts the flicker based upon the age of the user.

2. The method according to claim 1, wherein the at least one portion is in the middle of the display.

3. The method according to claim 1, wherein the at least one portion is around edges of the display.

4. The method according to claim 1, wherein the at least one portion is the entire display.

5. The method according to claim 1, wherein the at least one portion is a background on the display.

6. The method according to claim 1, wherein the at least one portion is information on the display.

7. The method according to claim 1, further comprising adjusting the flicker based upon a medical condition of the user.

8. The method according to claim 1, further comprising adjusting the flicker based upon a biological parameter of the user.

9. The method according to claim 1, further comprising adjusting the flicker based upon an ethnicity of the user.

10. A method for stimulating neural activity in the brain of a user of a smartphone with a display screen and that is capable of running apps, comprising the steps of:
    a. causing at least one portion of the display screen to flicker in a controlled manner, wherein the display screen is a touch-screen display;
    b. exposing the user of the smartphone to the flicker during an exposure time thereby producing an effect on the brain of the user; and
    c. adjusting the flicker by an app that is running on the smartphone, wherein the app adjusts the flicker based upon the gender of the user.

11. The method according to claim 10, wherein the at least one portion is in the middle of the display.

12. The method according to claim 10, wherein the at least one portion is around edges of the display.

13. The method according to claim 10, wherein the at least one portion is the entire display.

14. The method according to claim 10, wherein the at least one portion is a background on the display.

15. The method according to claim 10, wherein the at least one portion is information on the display.

16. The method according to claim 10, further comprising adjusting the flicker based upon a medical condition of the user.

17. The method according to claim 10, further comprising adjusting the flicker based upon a biological parameter of the user.

18. The method according to claim 10, further comprising adjusting the flicker based upon an ethnicity of the user.

19. A method for stimulating neural activity in the brain of a user of a smartphone with a display screen and that is capable of running apps, comprising the steps of:
    a. causing at least one portion of the display screen to flicker in a controlled manner, wherein the display screen is a touch-screen display;
    b. exposing the user of the smartphone to the flicker during an exposure time thereby producing an effect on the brain of the user; and c. adjusting the flicker by an app that is running on the smartphone, wherein the app adjusts the flicker based upon the race of the user.

20. The method according to claim 19, wherein the at least one portion is in the middle of the display.

21. The method according to claim 19, wherein the at least one portion is around edges of the display.

22. The method according to claim 19, wherein the at least one portion is the entire display.

23. The method according to claim 19, wherein the at least one portion is a background on the display.

24. The method according to claim 19, wherein the at least one portion is information on the display.

25. The method according to claim 19, further comprising adjusting the flicker based upon a medical condition of the user.

26. The method according to claim 19, further comprising adjusting the flicker based upon a biological parameter of the user.

27. The method according to claim 19, further comprising adjusting the flicker based upon an ethnicity of the user.

\* \* \* \* \*